United States Patent [19]

Laruelle et al.

[11] Patent Number: 4,804,684

[45] Date of Patent: Feb. 14, 1989

[54] SYMMETRICAL O-SUBSTITUTED DIOXIMES OF BENZO-FUSED β-DIKETOCYCLO-ALKYLENES, THE PROCESSES FOR THEIR PREPARATION AND THEIR APPLICATION AS DRUGS

[75] Inventors: Claude Laruelle, Villeneuve Loubet; Marcel Lepant, Nice; Bernard Raynier, Cagnes, all of France

[73] Assignee: Panmedica S.A., Carros, France

[21] Appl. No.: 4,576

[22] Filed: Jan. 20, 1987

[30] Foreign Application Priority Data

Jan. 29, 1986 [FR] France ................. 86 01223

[51] Int. Cl.$^4$ ............................................. A61K 31/15
[52] U.S. Cl. .................... 514/640; 558/422; 549/442; 549/407; 560/35; 562/440; 544/154; 546/203; 546/285; 514/456; 514/404; 514/524; 514/538; 514/561; 514/237; 514/325; 514/357; 564/257
[58] Field of Search ............... 568/326, 327; 564/257; 514/257, 456, 464, 524, 538, 540, 561, 237, 325, 357; 558/422; 549/442, 407; 560/35; 562/440; 544/154; 546/203, 285

[56] References Cited

U.S. PATENT DOCUMENTS

| | | | |
|---|---|---|---|
| 3,349,128 | 10/1967 | Judd | 564/257 |
| 3,621,101 | 11/1971 | Budai et al. | 514/640 |
| 3,784,606 | 1/1974 | Holland et al. | 568/327 |
| 3,903,164 | 9/1975 | Goransson-Dahlander et al. | 564/257 |
| 4,395,413 | 7/1983 | Budai et al. | 514/640 |
| 4,569,945 | 2/1986 | Campbell et al. | 568/327 |
| 4,605,673 | 8/1986 | Satzinger et al. | 564/379 |

OTHER PUBLICATIONS

Muceniece et al., Chem. Abst., vol. 77, #19338c, (1972).

*Primary Examiner*—James H. Reamer
*Attorney, Agent, or Firm*—Oblon, Fisher, Spivak, McClelland & Maier

[57] ABSTRACT

Drugs with high anticonvulsant and analgesic activities constituted by symmetrical β-dialkoxyiminocycloalklene derivatives in which the imine double bonds are conjugated with the cyclic double bond or bonds belonging to one or more fused benzene rings. They correspond to the general formula I:

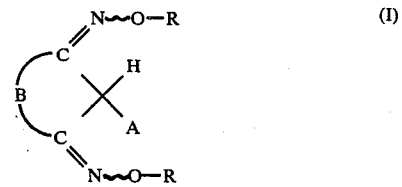

16 Claims, No Drawings

SYMMETRICAL O-SUBSTITUTED DIOXIMES OF BENZO-FUSED β-DIKETOCYCLO-ALKYLENES, THE PROCESSES FOR THEIR PREPARATION AND THEIR APPLICATION AS DRUGS

The present invention relates to novel symmetrical β-bis(alkoxyimino)cycloalkylene derivatives in which the two imine double bonds are conjugated with the cyclic double bond or bonds each belonging to a fused benzene ring.

They correspond to the following general formula:

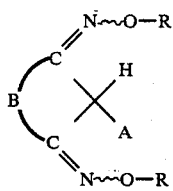

in which B represents the following unit;

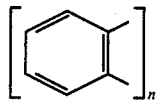

where n=1 or 2.

Thus, if B determines one double bond of a fused benzene ring, this being the case where n=1, a system of three conjugated double bonds (N=C—C=C—C=N) is in fact obtained:

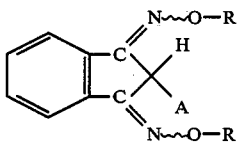

B may also determine a series of 2 double bonds of fused benzene rings, conjugated with one another and with the imine radicals, in which case a series of four conjugated double bonds (N=C—C=C—C=C—C=N) will be obtained:

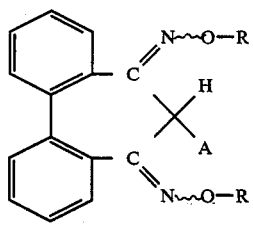

It is therefore seen that the cycloalkylene ring will contain five or seven carbon atoms.

In the first case, the two fused rings will determine an indane unit; in the second case, the three fused rings will represent a 6,7-dihydro-(5H)-dibenzo[a,c]cycloheptene.

Derivatives of the 2-phenylindane-1,3-dione type have been known for a long time and are used in human medicine as anticoagulants (phenindione); the homologs substituted on the 2-phenyl have been studied somewhat more recently and represent an advance in the therapy of anticoagulants (Fluindione).

Only the unsubstituted oximes have been synthesized, mainly for analytical purposes, and their pharmacological properties have not aroused any particular interest.

On the other hand, the tricyclic systems of the dibenzo[a,d]cycloheptene type have been very widely studied following the discovery of amitriptyline and its therapeutic properties in treating depression.

Thus, U.S. Pat. No. 3,270,055 to H. ENGELHARDT et al. describes derivatives obtained by dialkylaminoalkylation of the oxygen of the oxime of derivatives of 10,11-dihydrodibenzo[a,d]cyclohept-5-enes optionally substituted in the 3-position.

U.S. Pat. No. 3,349,128 (Colgate-Palmolive) also describes derivatives obtained by dialkylaminoalkylation of the oximes derived from dibenzo[a,d]cyclohept-5-enones optionally substituted in their phenyl nuclei.

These derivatives of oxygen can exist in the form of syn or anti isomers and are said to possess therapeutic properties as sedatives, antidepressants and muscle relaxants.

The tricyclic systems of the dibenzo[a,c]cycloheptene type have formed the subject of some earlier work.

GÖDECKE (European Patent No. 112.584) describes the 7-(aminoalkyl) or 7-(aminoalkoxy) derivatives of (5H)-dibenzo[a,c]cyclohept-5-enone as therapeutic agents for psychic diseases and gastric or intestinal ulcers.

In Chem. Ber. 104 (1971) 1573, RIED and CONTE describe the synthesis of 5,7-dioxo-6,7-dihydro-(5H)-dibenzo[a,c]cycloheptene and its unsubstituted dioxime.

The Applicant Company has found, surprisingly, that the bis-O-alkyloximes of beta-diketocycloalkenes containing double bonds which are completely conjugated and also form part of fused benzene rings have unexpected pharmacological properties.

The present invention relates to novel symmetrical β-dialkoxyiminocycloalkylene derivatives in which the imine double bonds are conjugated with the cyclic double bond or bonds belonging to one or more fused benzene rings.

They correspond to the following general formula (I):

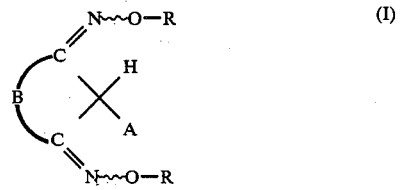

in which:
A represents hydrogen, a phenyl group or a phenyl group substituted by:
one or two halogen atoms such as fluorine, chlorine, bromine or iodine,
one or two lower alkyl radicals which can be a methyl, ethyl, propyl, isopropyl, cyclopropyl, n-butyl, sec.-butyl or tert.-butyl group,
one or two alkoxy radicals selected from the group comprising methoxy, ethoxy, propoxy, isopropoxy, butoxy and tert.-butoxy groups,
one or more substituents selected from the group comprising nitro, cyano, dimethylamino and diethylamino groups, several substituents selected from each of the different groups above, or
an o-methylenedioxy or o-ethylenedioxy group;

R represents:
- a linear or branched saturated or unsaturated alkyl radical containing from 1 to 16 carbon atoms,
- a cycloalkylalkyl or cycloalkyl radical which contains a total of 4 to 16 carbon atoms and whose ring contains from 3 to 8 carbon atoms,
- a phenyl or phenylalkyl radical, the alkyl unit containing from 1 to 3 methylene linkages,
- a linear or branched alkyl radical containing from 1 to 6 carbon atoms and substituted by a group —$NR_1R_2$, where $R_1$ and $R_2$, which are identical or different, are hydrogen atoms or linear or branched alkyl groups containing from 1 to 4 carbon atoms and optionally substituted by a hydroxyl, methoxy or ethoxy group, or alternatively $R_1$ and $R_2$, which are identical or different, can determine a saturated or unsaturated nitrogen heterocycle or a saturated or unsaturated heterocycle containing a nitrogen atom and a heteroatom which can be sulfur, oxygen or nitrogen, the said heterocycle being optionally substituted,
- a heterocycle containing from 5 to 7 ring members and 1 or 2 heteroatoms selected from the group comprising nitrogen, sulfur and oxygen, the said heterocycle being connected by a methylene linkage containing from 1 to 4 carbon atoms, or
- a saturated or unsaturated linear or branched alkyl radical containing from 1 to 16 carbon atoms and substituted by:
  - a group CN or
  - a group —COOQ, Q being hydrogen, a linear or branched alkyl radical containing from 1 to 6 carbon atoms or a phenylmethyl or phenyl radical, these phenyl rings being optionally substituted by a halogen, a cyano group, a methyl group, a methoxy group or a trifluoromethyl group; and B represents the linkage:

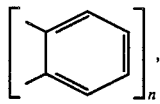

n being equal to 1 or 2, one double bond of a fused benzene nucleus, or two double bonds which are conjugated with one another and with the imino groups and are each included in a fused benzene nucleus,
and their pharmacologically acceptable salts in cases where R contains a salifiable group.

Therefore, in the general formula I, B will determine an O-substituted β-dioxime of indane-1,3-dione when n=1 and an O-substituted β-dioxime of 5,7-dioxodibenzo[a,c]cycloheptene when n=2.

The present invention relates to all the geometric isomers—ZZ, EE, ZE (Z denoting syn and E denoting anti)—which are generated by the linkages C=N—O—R, or to any one of the isomers obtained in the pure state by a conventional method of separation, such as column chromatography, from the mixture of isomers.

The derivatives of the general formula (I) have valuable medicinal properties. Their pharmacological activities are demonstrated by means of the following standard tests:

Anticonvulsant activity in mice

One hour after oral administration of the test product to mice, 50 mg/kg of pentamethylenetetrazole are injected intravenously.

The anticonvulsant activity is measured by the reduction in or suppression of the animals' tonic extensions. The $ED_{50}$ of the derivatives according to the invention (the effective dose which reduces convulsions by 50%) varies from 200 to 5 mg/kg.

Analgesic activity in rats

The writhing test is performed on rats by Koster's method (Fed. Proc. 18, 412, (1959)). When administered in an amount of 100 mg/kg, some derivatives according to the present invention exhibit a good analgesic activity.

Antagonistic effects on isolated guinea-pig intestine

In the test described by MAGNUS (Arch. F.D. Ges. Physiol. 102–123), with the perfusion medium containing 10 μg of product/ml, the derivatives according to the invention are found to be antagonized by serotonin, acetylcholine, histamine and barium chloride.

For some derivatives, in particular those described in Examples 14, 15, 16, 17, 18, 19 and 22, this inhibitory effect is still substantial at a concentration of 0.1 μg/ml.

In vitro inhibition of platelet aggregation

The inhibition of platelet aggregation is measured in vitro by BORN's method (Nature 4832, 927 (1962)), the aggregation being induced by collagen or ADP.

The derivatives according to the present Application, tested at a concentration of 100 μg/ml, are comparable or even superior to aspirin, which is taken as the reference, especially in the case of the products described in Examples 15, 16, 17, 18, 19, 20, 21, 24, 25, 26, 27, 28, 29, 30, 32, 33, 34 and 35. The aggregation can also be induced in vitro by serotonin, arachidonic acid and norepinephrine. Furthermore, this inhibitory effect was observed on platelet-rich plasma (PRP) of animal origin and human origin.

Ex vivo activity on clotting and on the platelet aggregation induced by ADP and collagen in rats, after 6 days of administration The products all proved active in this test, but the intensity and duration of action (different ½-life) were variable.

Prolongation of the bleeding time

The study is carried out in vitro on rats and shows a significant prolongation of the bleeding time after a single oral administration of the derivatives according to the invention.

Thrombolytic activity towards experimental arterial or venous thrombi after oral administration to rats

Antiinflammatory activity on rat paw edema induced by carrageenin

The activities of the derivatives according to the invention are variable but many of them are comparable or even superior to the activity induced by aspirin.

General in vitro tests on hemostasis, including the kaolin-activated partial thromboplastin time (relates to factors I, II, V, VIII, IX, X, XI and XII)

The thrombin clotting time, which measures the conversion of fibrinogen to fibrin The response to these tests is excellent for all the derivatives of the invention.

The derivatives of the formula (I) in which R represents a hydrocarbon radical substituted by a basic group are converted to pharmacologically acceptable salts by neutralization with an organic or inorganic acid, for example hydrochloric, sulfuric, hydrobromic, phosphoric, methanesulfonic, hydroxyethanesulfonic, acetic, propionic, fumaric, oxalic, malic, lactic, citric, tartaric, ascorbic, maleic, succinic, aspartic, glutamic, acetylaminoacetic, acetylaspartic or pyroglutamic acid.

The derivatives of the formula I in which R represents a hydrocarbon radical substituted by a carboxyl group are converted to pharmacologically acceptable salts by neutralization with an organic or inorganic base, for example sodium hydroxide, potassium hydroxide, aqueous ammonia, magnesium hydroxide, calcium hydroxide, triethylamine, isopropylamine, ethanolamine, diethylaminoethanol, dimethylaminoethanol, piperazine, N-methylpiperazine or morpholine.

The pharmaceutical compositions can be converted to forms suitable for oral administration (for example tablets, pills, coated tablets, capsules or syrup) or parenteral administration (for example injectable solutions). It is possible to add inert substances such as starch, lactose, mannitol, ethyl cellulose, talc, a dispersing agent or an agent for assisting compression.

These substances are added by the methods known per se in the pharmaceutical industry.

Another characteristic of the present invention is the use of the derivatives of the formula I and their addition salts in human or veterinary therapy for the treatment of complaints resulting from an irregularity in the platelet function and the blood aggregation, and complaints of the central nervous system, and also as analgesics and antiinflammatories. The desirable daily dose is about 0.1 to 200 mg/kilo of body weight, preferably from 1 to 50 mg/kg, administered in a single dose or in divided doses taken between 2 and 4 times a day.

A delayed-action form can also be produced in order to avoid repeat doses.

Among the numerous compounds described in the invention, attention is drawn to the particularly powerful pharmacological activities of the derivatives of the general formula (I) in which R represents a linear alkyl radical substituted by a group $NR_1R_2$, and more especially the 5,7-bis(2-aminoethoxyimino), 5,7-bis(3-aminopropoxyimino) and 5,7-bis(2-diethylaminoethoxyimino) derivatives of (5H)-dibenzo[a,c]cycloheptene, substituted or unsubstituted in the 6-position, and the same symmetrical oxime derivatives of 2-phenylindane-1,3-dione.

The present Application also relates to a process for the synthesis of derivatives of the formula I.

The compounds corresponding to the formula I are obtained by reacting the corresponding β-diketocycloalkenes, i.e. 2-phenyl-(1H)-indene-1,3(2H)-dione or 6,7-dihydro-(5H)-dibenzo[a,c]cycloheptene-5,7-dione of the formula (II), with the hydrohalide of an O-substituted hydroxylamine of the formula III, according to the following reaction scheme:

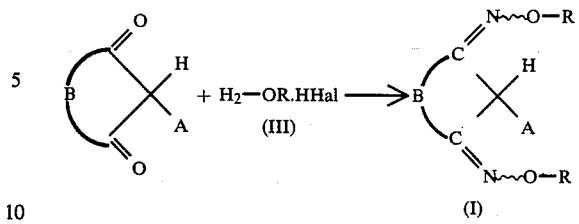

in which R has the meanings indicated above and Hal denotes chlorine or bromine.

This reaction is carried out in a solvent which can be pyridine or an alcohol containing from 1 to 3 carbon atoms, which is anhydrous or aqueous, or a mixture of pyridine and alcohol.

In an aqueous medium, it is desirable to use a base selected from the group comprising sodium or potassium acetate, sodium or potassium carbonate and calcium or magnesium hydroxide.

The reaction is preferably carried out in absolute ethanol at the boiling point.

When they are not commercially available, the O-substituted hydroxylamines can be synthesized by reacting N-hydroxyphthalimide with the commercially available halogen derivatives Hal-R, according to the following reaction scheme:

where the O-substituted derivative of N-hydroxyphthalimide V is prepared by reacting the latter with the derivative Hal-R, in which Hal is a halogen, preferably bromine or chlorine, in solution in a solvent such as dimethylformamide, acetonitrile or dimethyl sulfoxide, in the presence of a base such as triethylamine or an alkali metal carbonate, at a temperature of between 20° and 120° C.

The reaction will preferably be carried out in dimethylformamide, in the presence of triethylamine, at between 100° and 110° C.

The O-substituted hydroxylamine is prepared from the derivative V by removal of the phthalimido protecting group. This removal can be effected by hydrazinolysis in solution in a lower alcohol and at the reflux temperature.

It is preferred to use the theoretical quantity of hydrazine hydrate in solution in ethanol. The addition of concentrated hydrochloric acid gives the hydrochloride of the O-substituted hydroxylamine.

The O-substituted hydroxylamines III in which R represents a linear or branched alkyl group substituted by a group —NR$_1$R$_2$ can also advantageously be prepared according to a slightly different reaction scheme.

The alkylation of N-hydroxyphthalimide with an ω,ω'-dibromoalkane by the method of L. BAUER, J. Org. Chem. (1963), 28, p. 1604, provides access to the ω-brominated derivative of the product of the general formula V.

When treated with a secondary amine HNR$_1$R$_2$, this derivative gives the product of the general formula V in which R represents a linear or branched alkyl group substituted by a group —NR$_1$R$_2$.

This reaction is preferably carried out with two equivalents of amine HNR$_1$R$_2$ or with one equivalent of amine HNR$_1$R$_2$ and any other acid acceptor selected from the group comprising pyridine, triethylamine, collidine and sodium or potassium carbonate.

This reaction is carried out in the presence of a solvent such as benzene, toluene, xylene, acetonitrile or, more advantageously, acetone, butan-2-one or 3-methylbutan-2-one, at a temperature of between 40° and 130° C., most commonly at the reflux temperature of the chosen solvent.

The phthalimido protecting group can be removed by hydrazinolysis, as mentioned previously, or by acid hydrolysis with 6N hydrochloric acid, by itself or in the presence of acetic acid, at the reflux temperature.

The resulting O-substituted hydroxylamine of the general formula III is isolated in the form of the hydrochloride.

The compounds of the formula III can also be prepared by reacting the halogen derivative Hal-R (IV) with another hydroxylamine precursor protected on the nitrogen, and then removing the protecting group in the conventional manner.

Among the other precursors used which are different from N-hydroxyphthalimide, there may be mentioned benzohydroxamic acid, N-hydroxyurethane or, preferably, t-butyl N-hydroxycarbamate or acetone oxime.

If an isopropylidene or α-hydroxybenzylidene group is used, the reaction is carried out in the presence of a basic agent, for example a sodium alcoholate in the corresponding alcohol or an alkali metal carbonate in an aromatic hydrocarbon, preferably benzene.

If an isopropylidene, α-hydroxybenzylidene or carbalkoxy group is used, the protecting group is removed by acid hydrolysis.

If, in a formula III, R represents a carboxyalkyl group of the type:

H$_2$N—O—(CH$_2$)$_m$—COOH, a protecting group for the carboxyl functional group has to be used for the reaction with N-hydroxyphthalimide, the said protecting group being more precisely an ester of a lower alkyl selected from the group comprising methyl, ethyl, propyl, isopropyl and tert.-butyl radicals, or a benzyl ester.

After the preparation of the derivative of the formula (I) in which R represents a unit:

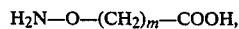
—(CH$_2$)$_m$—COO—lower alkyl or

—(CH$_2$)$_m$—COO—benzyl, the derivative of the formula (I) in which R represents the unit:

—(CH$_2$)$_m$—COOH can be obtained by alkaline hydrolysis in the case of the methyl, ethyl or propyl ester. This hydrolysis can be performed in an aqueous-alcoholic mixture containing a slight excess of an alkali metal hydroxide, the reaction being carried out between ordinary temperature and the reflux temperature, preferably at between 40 and 60 degrees C. The hydrolysis of the tert.-butyl ester is preferably effected with trifluoroacetic acid.

In the case where R represents a unit:

—(CH$_2$)$_m$—COO—benzyl, the benzyl group can be removed by alkaline hydrolysis as above, or by hydrogenolysis in the presence of a palladium catalyst in solution in a lower alkanol, preferably isopropanol.

If, in the formula III:

NH$_2$—O—R,

R represents a hydrocarbon radical substituted by a primary or secondary amine, i.e. a hydrocarbon radical carrying one or two mobile hydrogens, this functional group has to be protected, during the synthesis of the O-substituted hydroxylamine, by the procedure given below; R=Y—NH—R$_8$, in which Y is a linear, branched or cyclic hydrocarbon unit and R$_8$ is hydrogen or a lower alkyl radical.

An α-halogeno-ω-amino or alkylaminoalkyl derivative is reacted with benzyloxycarbonyl chloride in stoichiometric amounts.

The reaction is carried out in an organic solvent or in water, in the presence of a mineral base and at a temperature of between 0° and 50° C.

The reaction will preferably be carried out in solution in normal sodium hydroxide containing 10% of acetone and at ordinary temperature.

After evaporation of the solvent, acidification and extraction, the N-benzyloxycarbonylamino derivative is reacted according to the process described above.

This gives the derivatives of the formula I in which R contains a benzyloxycarbonyl group protecting the reactive nitrogen atom.

The amine functional groups are then freed by hydrogenolysis in solution in a lower alkanol, in the presence of a palladium catalyst, in the presence of hydrogen at a pressure of between 0 and 20 bar and at a temperature of between 20° and the boiling point, the medium being neutral or slightly acidic.

The reaction will preferably be carried out in solution in ethanol, in the presence of a 5% palladium-on-charcoal catalyst and in the presence of hydrogen at atmospheric pressure, with the theoretical amount of hydrochloric acid in order to form the hydrochloride of the freed amines.

The examples which follow make it possible to describe the scope of the present invention without implying a limitation. The products obtained were subjected to elemental analysis and correspond to the calculated theoretical percentages to within 0.3%.

The purity of the compounds according to the invention was checked by thin layer chromatography on a silica gel F 254 plate with the following elution systems:
A: toluene 10 - formic acid 1 - ethyl formate 10
B: n-butanol 8 - acetic acid 1 - water 1
C: benzene 70 - methanol 0.5
D: n-butanol 1 - acetic acid 1 - water 1 ethyl acetate 1

EXAMPLE 1

5,7-Bis(Allyloxyimino)-6,7-Dihydro-(5H)-Dibenzo[a,c]Cycloheptene

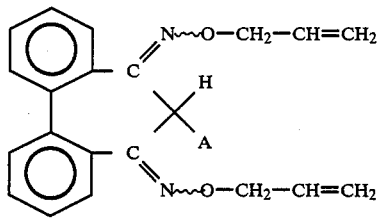

(a) Allyloxyamine hydrochloride 81.5 g (0.5 mol) of N-hydroxyphthalimide are added to 300 ml of dimethylformamide, and 83 ml of triethylamine are then introduced at ordinary temperature. 50 ml (0.6 mol) of allyl bromide are run into the colored solution obtained, the mixture is then heated at 100°/110° C. for 5 hours and cooled and the triethylamine hydrobromide is filtered off at ordinary temperature. The filtrate is evaporated to dryness under reduced pressure, the residue is taken up in chloroform and the mixture is then washed with water. After evaporation, 95% of O-allyloxyphthalimide are obtained—m.p.=60° C.; this is dissolved in 450 ml of ethanol into which 27 ml of hydrazine hydrate (0.55 mol) are run over a period of a few minutes.

The mixture is subsequently heated under reflux for 3 hours, with vigorous stirring, and cooled to about 0° C. and 6.4 ml of concentrated hydrochloric acid are then run in slowly. The allyloxyamine hydrochloride is left to crystallize in the cold and then filtered off; it can be recrystallized from alcohol to give attractive white crystals with a yield of 90% relative to the hydroxyphthalimide.

(b) 5,7-Bis(allyloxyimino)-6,7-dihydro-(5H)-dibenzo[a,c]cycloheptene-5,7-dione 12.5 g (0.114 mol) of allyloxyamine hydrochloride, prepared according to a, are added to 250 ml of ethanol containing 12.67 g (57 mmol) of 6,7-dihydro-(5H)-dibenzo[a,c]cycloheptene-5,7-dione and the mixture is heated under reflux for a few hours until the starting material has disappeared.

The mixture is evaporated and the residue is purified by chromatography on silica with benzene to give the title derivative consisting of a mixture of the various isomers: Z,E, E,E and Z,Z. The yield is 75% relative to the dione.

The physicochemical characteristics are as follows:
NMR (in CDCl$_3$/TMS): 7.4 ppm (s) 8H (arom), 5.7/6.2 ppm (m) 1H (CH—CH$_2$), 5.0/5.3 ppm (m) 2H (CH=CH$_2$), 4.6 ppm (m) 2H (—OCH$_2$), 4.25 ppm (s) 2H (—$\overline{\text{CH}}_2$—) for the symmetrical isomer. The asymmetrical E,Z isomer gives a complex unresolved signal at 7.4 ppm 8H (arom) and a less deshielded singlet at 4.0 ppm 2H (—CH$_2$). The ratio of the intensities of the signals for the ring —CH$_2$— makes it possible to determine the respective % of the symmetrical and asymmetrical isomers. IR (in KBr): 1600 and 1645 cm$^{-1}$ (sharp), 1440 cm$^{-1}$ (s), 1030 and 930 cm$^{-1}$ (vs) =N—O—.

EXAMPLE 2

5,7-Bis(Methoxyimino)-6,7-Dihydro-(5H)-Dibenzo[a,c]Cycloheptene 5 g (59.9 mmol) of commercial methoxyamine hydrochloride are added to a solution of 6.5 g (29.3 mmol) of 6,7-dihydro-(5H)-dibenzo[a,c]cycloheptene-5,7-dione in 160 ml of ethanol. The mixture is then treated under the conditions of Example 1-b. The crude evaporation product is recrystallized from isopropanol to give a first crop of 57% of a white product melting at 130°/136° C. and containing more than 90% of a pure isomer (TLC system A—Rf=0.90—the starting diketone is at Rf=0.7).

NMR: 7.4 ppm (s) 8H (arom), 4.20 ppm (s) (—CH$_2$—), predominant isomer 3.75 ppm (s), traces of the second isomer, 3.85 ppm (s) 6H (—OCH$_3$).

A second crop of 20% of a product melting at 140° C. and consisting of a pure isomer brings the overall yield to 77%.

EXAMPLE 3

5,7-Bis(Ethoxyimino)-6,7-Dihydro-(5H)-Dibenzo[a,c]Cycloheptene

Following the operating conditions of Example 1-b and using ethoxyamine hydrochloride gives the title derivative with a yield of 90%; in TLC, it shows the two spots for the symmetrical and asymmetrical isomers, respectively at Rf=0.87 and 0.80 in system A or at Rf=0.42 and 0.27 in benzene only. The melting point is 112° C.

After several crystallizations from isopropyl alcohol, the isomer of higher Rf is gradually converted to the other isomer of lower Rf, which then melts at 118° C.

NMR 7.4 ppm (s) 8H (arom), 4.25 ppm (s) 2H (—CH$_2$—), 4.20 ppm (q) 4H (O—CH$_2$—CH$_3$), 1.25 ppm (t) 6H (O—CH$_2$—CH$_3$).

EXAMPLE 4

5,7-Bis(n-Propoxyimino)-6,7-Dihydro-(5H)-Dibenzo[a,c]Cycloheptene (a) n-Propoxyamine hydrochloride Following the procedure of Example 1-a and using 1-bromopropane in place of the allyl bromide gives n-propoxyamine hydrochloride in the form of white crystals melting at 155/6° C. with a yield of 80% relative to the phthalimide.

(b) Di(O-n-propyloxime) of 6,7-dihydro-(5H)-dibenzo[a,c]cycloheptene-5,7-dione

Following the conditions of Example 1-b gives, after purification on a silica column with benzene, the title derivative in the form of a yellow oil with a yield of 75% relative to the N-hydroxyphthalimide.

In TLC, the product shows a double spot of Rf=0.92 in system A. In benzene only, TLC makes it possible to differentiate between two spots of identical size at Rf=0.45 and 0.55.

NMR: 7.4 ppm (s) and (m), total of 8H (arom), 4.25 and 4.05 ppm, two (s) of identical intensity, total of 2H (—CH$_2$—), 4.0 ppm (m) 4H (OC$\underline{H}_2$—CH$_2$), 1.55 ppm (m) 4H (OCH$_2$—C$\underline{H}_2$—CH$_3$), 0.9 ppm (m) 6H (OCH$_2$—CH$_2$—C$\underline{H}_3$).

EXAMPLE 5

5,7-Bis(3-Cyanopropoxyimino)-6,7-Dihydro-(5H)-Dibenzo[a,c]Cycloheptene (a) 3-Cyanopropoxyamine hydrochloride Following the operating conditions of Example 1-a and using 4-n-bromobutyronitrile instead of the ally bromide gives, after crystallization from isopropyl ether, O—(3-cyanopropyl)hydroxylamine hydrochloride with a yield of 95% relative to the hydroxyphthalimide, in the form of white crystals melting at 134°/136° C.

(b) Di[O—(3-cyanopropyl)oxime] of 6,7-dihydro-(5H)-dibenzo[a,c]cycloheptene-5,7-dione Using the operating conditions of Example 1-b with the hydroxylamine previously obtained in 5-a gives the title derivative, which is purified by chromatography on a silica column with a chloroform/acetone mixture. The title derivative is thus obtained in the form of a thick oil with a yield of 70% (relative to the dione); in TLC, it shows a slightly resolved spot of Rf=0.65 in system A and two spots of identical intensity at Rf=0.05 and 0.15 in the system benzene 100/methanol 0.5, corresponding to the symmetrical and asymmetrical isomers.

EXAMPLE 6

5,7-Bis(Tert.-Butoxyimino)-6,7-Dihydro-(5H)-Dibenzo[a,c]Cycloheptene

Following the conditions of Example 1-b and starting from t-butoxyamine hydrochloride gives 82% of the title derivative in the form of white crystals melting at 181°-3° C.; in TLC, it shows a single spot of Rf=0.95 in system A and also a single spot of Rf=0.85 in benzene alone.

NMR: 7.4 ppm (s) 8H (arom), 4.2 ppm (s) 2H (—CH$_2$—), 1.25 ppm (s) 18H (t-but.).

EXAMPLE 7

5,7-Bis(Cyclohexylmethoxyimino)-6,7-Dihydro-(5H)-Dibenzo[a,c]Cycloheptene (a) Cyclohexylmethoxyamine hydrochloride Following the procedure of Example 1-a and using bromomethylcyclohexane in place of the allyl bromide gives O-cyclohexylmethylhydroxylamine hydrochloride in the form of white crystals melting at 173° C. with a yield of 70% relative to the phthalimide.

(b) Di(O-cyclohexylmethyloxime) of 6,7-dihydro-(5H)-dibenzo[a,c]cycloheptene-5,7-dione Following the conditions of Example 1-b gives the title derivative with a yield of 91% relative to the dione. Recrystallization from chloroform produces a first crop of a pure isomer melting at 97°/99° C.

NMR: 7.4 ppm (s) 8H (arom), 4.2 ppm (s) 2H (—CH$_2$—), 3.90 ppm (d) (J=6 Hz) 4H (—OCH$_2$—), 1.8 to 1.0 ppm (m) 22H.

EXAMPLE 8

5,7-Bis(Benzyloxyimino)-6,7-Dihydro-(5H)-Dibenzo[a,c]Cycloheptene

Following the procedure described in Example 1-b and using O-benzylhydroxylamine hydrochloride in place of the allyloxyamine hydrochloride gives the title derivative melting at 112°/114° C. with a yield of 81% relative to the starting dione; in TLC, it shows a spot of Rf=0.95 in system A and 0.80 in a 70/0.2 benzene/methanol mixture.

EXAMPLE 9

5,7-Bis(2-Phenylethoxyimino)-6,7-Dihydro-(5H)-Dibenzo[a,c]Cycloheptene (a) O-Phenethylhydroxylamine hydrochloride Following the procedure indicated in Example 1-a and using phenethyl bromide instead of the allyl bromide gives 2-phenylethoxyamine hydrochloride in the form of white crystals with a yield of 91%.

(b) 5,7-Bis(2-phenylethoxyimino)-6,7-dihydro-(5H)-dibenzo[a,c]cycloheptene

Using O-phenethylhydroxylamine, prepared according to a, under the conditions of Example 1-b gives, after chromatography on silica with benzene, the title derivative in the pure state as a thick oil with a yield of 85%; it is a mixture of the isomers.

NMR: 7.4 ppm (s) 8H (arom), 7.2 ppm (s) 10H (arom), 4.2 and 3.9 ppm (2s) (—CH$_2$—), 4.25 ppm (m) 4H (OCH$_2$), 2.9 ppm (m) 4H (O—CH$_2$—CH$_2$—).

EXAMPLE 10

5,7-Bis(Ethoxycarbonylmethoxyimino)-6,7-Dihydro-(5H)-Dibenzo[a,c]Cycloheptene (a) O-Ethoxycarbonylmethylhydroxylamine hydrochloride Using ethyl bromoacetate in place of the allyl bromide and following the conditions of Example 1-a gives ethoxycarbonylmethoxyamine hydrochloride in the form of white crystals melting at 106° C. with a yield of 91%.

(b) Di(O-ethoxycarbonylmethyloxime) of 6,7-dihydro-(5H)-dibenzo[a,c]cycloheptene-5,7-dione Following the conditions of Example 1-b and starting from the above hydroxylamine gives, after purification by chromatography in chloroform, 55% of the title derivative in the form of white crystals melting at 95° C.; in TLC, it shows two spots of Rf=0.60 and 0.65 in the system chloroform/acetone 70/1, corresponding to the two isomers.

NMR: 7.4 ppm (s) 8H (arom), 4.65 ppm (s) 4H (—OCH$_2$COO), 4.45 ppm (d) and 4.0 ppm (s) 2H (—C$\underline{H}_2$—), mixture of the isomers, 4.1 ppm (q) 4H (—C$\underline{H}_2$CH$_3$), 1.15 ppm (t) 6H (OCH$_2$C$\underline{H}_3$).

EXAMPLE 11

5,7-Bis(Tert.-Butoxycarbonylmethoxyimino)-6,7-Dihydro-(5H)-Dibenzo[a,c]Cycloheptene (a) O-t-Butoxycarbonylmethylhydroxylamine hydrochloride Using t-butyl bromoacetate under the conditions of Example 1-a gives tert.-butoxycarbonylmethoxyamine hydrochloride in the form of white crystals melting at 98° C. with a quantitative yield.

(b)
5,7-Bis(tert.-butoxycarbonylmethoxyimino)-6,7-dihydro-(5H)-dibenzo[a,c]cycloheptene Following the conditions of Example 1-b and starting from the hydroxylamine prepared above gives the title derivative in the form of white crystals melting at 105°–107° C. with a yield of 65% relative to the dione.

NMR: 7.4 ppm (m) 8H (arom), 4.5 ppm (s) 4H (OCH$_2$CO), 4.3 ppm (d) and 4.1 ppm (s) 2H (—CH$_2$—), mixture of the isomers, 1.40 ppm (s) 18H (t-but.).

In TLC, the product shows a single spot of Rf=0.87 in system A.

EXAMPLE 12

5,7-Bis(Ethoxycarbonylpropoxyimino)-6,7-Dihydro-(5H)-Dibenzo[a,c]Cycloheptene (a) O-(Ethoxycarbonylpropyl)hydroxylamine hydrochloride Following the conditions of Example 1-a and starting from ethyl 4-bromobutyrate gives ethoxycarbonylpropoxyamine hydrochloride in the form of white crystals melting at 99° C. with a yield of 75% relative to the N-hydroxyphthalimide.

(b)
5,7-Bis(ethoxycarbonylpropoxyimino)-6,7-dihydro-(5H)-dibenzo[a,c]cycloheptene Following the procedure of 1-b with the hydroxylamine prepared above gives the title derivative in the form of a thick oil with a yield of 80%; in TLC, it shows a single spot in system A and the two spots for the symmetrical and asymmetrical isomers at Rf=0.55 and 0.60, respectively, in benzene.

NMR: 8.4 ppm (s broad) 8H (arom), 4.25 to 3.90 ppm (complex m) 10H (—CH$_2$—, OCH$_2$—CH$_2$, —COOCH$_2$), 2.5 to 1.8 ppm (m) 8H (CH$_2$—CH$_2$—CO), 1.25 ppm (t) 6H (O—CH$_2$—CH$_3$).

EXAMPLE 13

5,7-Bis(Hydroxycarbonylmethoxyimino)-6,7-Dihydro-(5H)-Dibenzo[a,c]Cycloheptene 13 mmol (6.6 g) of the tert.-butyl ester described in Example 11 are added to 40 ml of trifluoroacetic acid. After two hours at ordinary temperature, the mixture is evaporated under reduced pressure and the residue is taken up in ether and then in petroleum ether.

This gives the title derivative in the form of white crystals melting at 185° C. with a quantitative yield; in TLC, it shows a single spot of Rf=0.45 in system A and a slightly resolved spot of Rf=0.70 in system B.

NMR: 7.4 ppm (s) 8H (arom), 4.70 ppm (s) 4H (—O—CH$_2$—CO—), 4.5 and 4.1 ppm (d) and (s) 2H (—CH$_2$—), isomers at 10.8 ppm 2H exchangeable.

EXAMPLE 14

5,7-Bis(Pyridin-3-ylmethoxyimino)-6,7-Dihydro-(5H)-Dibenzo[a,c]Cycloheptene Dihydrochloride (a) O-(Pyridin-3-Ylmethyl)hydroxylamine hydrochloride The conditions of Example 1-a are followed using 3-chloromethylpyridine hydrochloride. However, at the end of the operation and before taking up the product in chloroform, the aqueous solution is rendered alkaline with sodium hydroxide solution to give N-(picol-3-yloxy)phthalimide as the base. The usual treatment produces O-(picol-3-yl)hydroxylamine hydrochloride in the form of white crystals melting at 182° C.

(b)
5,7-Bis(pyridin-3-ylmethoxyimino)-6,7-dihydro-(5H)-dibenzo[a,c]cycloheptene dihydrochloride Following the conditions of Example 1-b and using the hydroxylamine prepared above gives 5,7-bis(pyridin3-ylmethoxyimino)-6,7-dihydro-(5H)-dibenzo[a,c]cycloheptene, which is purified by chromatography on alumina in chloroform.

The pure product is dissolved in 2 volumes of ethanol and treated with the theoretical amount of anhydrous hydrochloric acid; the addition of ether gives the title derivative in the form of white crystals melting at 130° C. with a yield of 70% relative to the dione; in TLC, it shows a single spot of Rf=0.60 in system B (the dione is at 0.95) and also a single spot on alumina in chloroform.

NMR: 9 to 7.4 ppm (m) 18H (arom), 5.4 ppm (s) 4H (—OCH$_2$—), 5.2 and 4.4 ppm (s) 2H (—CH$_2$—).

EXAMPLE 15

5,7-Bis(2-Diethylaminoethoxyimino)-6,7-Dihydro-(5H)-Dibenzo[a,c]Cycloheptene Dihydrochloride (a) 2-Diethylaminoethoxyamine hydrochloride from isopropylidenehydroxylamine 73 g of acetone oxime are dissolved in 250 ml of benzene, 17.5 g of diethylaminochloroethane hydrochloride are added, 350 g of dry potassium carbonate are then introduced cautiously at ordinary temperature, with vigorous stirring, and the mixture is subsequently heated under reflux for 10 hours.

The suspension is filtered and the organic solution is extracted with an excess of dilute hydrochloric acid. The hydrochloric acid solution is then heated to 60° C., with thorough stirring, and the pressure is gradually lowered in order to distil the acetone produced and the excess water.

Cooling and the addition of ethanol cause diethylaminoethoxyamine dihydrochloride to crystallize.

(b) Using the conditions of Example 14-b with 2-diethylaminoethoxyamine hydrochloride gives the title derivative in the form of a yellow oil. Dissolution in ethanol, addition of the theoretical amount of anhydrous hydrochloric acid and taking-up of the product in ether gives 5,7-bis(2-diethylaminoethoxyimino)-6,7-dihydro-(5H)dibenzo[a,c]cycloheptene dihydrochloride in the form of white crystals melting at 173° C.; in TLC, it shows two spots of Rf=0.38 and 0.25 in system B, corresponding to the two isomers.

NMR: 7.5 ppm (m) 8H (arom), 4.5 ppm (m) 4H (O—CH$_2$—CH$_2$), 4.4 and 3.9 ppm (s) 2H (—CH$_2$—), isomers, 3.5 to 2.8 ppm (m) 12H (—N—CH$_2$—), 1.2 ppm (t) 6H (—CH$_2$—CH$_3$).

The organic acid salts of the base prepared according to Example 15 can be prepared by mixing, in a molar ratio of 1 to 2, the base and the organic acids normally used to salify therapeutically active molecules of basic character; the following derivatives are obtained in this way:

EXAMPLE 16

5,7-Bis(2-Diethylaminoethoxyimino)-6,7-Dihydro-(5H)-Dibenzo[a,c]Cycloheptene Dimaleate Salification in isopropanol gives the title derivative in the form of an amorphous mass melting at 74° C.

EXAMPLE 17

5,7-Bis(2-Diethylaminoethoxyimino)-6,7-Dihydro-(5H)-Dibenzo[a,c]Cycloheptene Ditartrate This is recrystallized from isopropanol containing 1% of water to give attractive white crystals melting at 60° C.

The difumarate (m.p.=70° C.) is obtained in the same manner.

EXAMPLE 18

5,7-Bis(2-Aminoethoxyimino)-6,7-Dihydro-(5H)-Dibenzo[a,c]Cycloheptene Dihydrochloride (a) 2-Benzyloxycarbonylaminoethoxyamine hydrochloride A solution of 0.46 mol (78.5 g) of benzyloxycarbonyl chloride in 1 volume of acetone is added slowly to a solution of 0.45 mol (92.2 g) of 2-bromoethylamine in 1 liter of nomal sodium hydroxide solution. When the reaction has ended (about 48 hours), the acetone is evaporated off under reduced pressure and the residue is then acidified to between pH 1 and 2 and extracted with ether. Benzyloxycarbonylamino-2-bromoethane is obtained after evaporation. This product is reacted with N-hydroxyphthalimide following the procedure of Example 1-a to give N-2-benzyloxycarbonylaminoethoxyphthalimide in the form of white crystals melting at 95° C. with a yield of 73%. After treatment with hydrazine under the conditions of Example 1-a, 2-benzyloxycarbonylaminoethoxyamine hydrochloride melting at 178° C. is obtained (yield=95% relative to the phthalimide).

(b) 5,7-Bis(2-benzyloxycarbonylaminoethoxyimino)-6,7-dihydro-(5H)-dibenzo[a,c]cycloheptene Following the operating conditions of Example 1-b and using the hydrochloride of the oxyamine prepared above gives the title derivative with a yield of 75% after purification on a silica column in chloroform. The product, which is a mixture of the isomers, is in the form of a thick oil.

NMR: 7.4 ppm (m) 18H (arom), 5.1 ppm (s) 4H (COO$\underline{CH_2}$), 4.8 and 4.0 ppm (m) 2H (—CH$_2$—), 4.2 ppm (t) 4H (—O$\underline{CH_2}$—CH$_2$), 3.5 ppm (q) 4H (—NCH$_2$—).

(c) 5,7-Bis(2-aminoethoxyimino)-6,7-dihydro-(5H)-dibenzo[a,c]cycloheptene dihydrochloride The product obtained in the previous section is subjected to hydrogenolysis in an ethanolic solution of hydrochloric acid, in the presence of 5% palladium-on-charcoal. When diluted with ether, the alcoholic solution yields the title derivative in the form of attractive white crystals melting at 210° C.; in TLC, it shows a spot of Rf=0.50 in system B.

NMR: 7.4 ppm (s) 8H (arom), 4.5 ppm (s) and 4.1 ppm (m) 2H (—CH$_2$—) (isomers), 4.3 ppm (m) 4H (—O$\underline{CH_2}$—CH$_2$), 3.2 ppm (m) 4H (—NH$_2$—$\underline{CH_2}$).

EXAMPLE 19

5,7-Bis(3-Aminopropoxyimino)-6,7-Dihydro-(5H)-Dibenzo[a,c]Cycloheptene Dihydrochloride (a) 3-Benzyloxycarbonylaminopropoxyamine hydrochloride Following the conditions of Example 18-a and using 3-bromopropylamine in place of the 2-bromoethylamine gives benzyloxycarbonylamino-3-bromopropane. When reacted with N-hydroxyphthalimide under the conditions of Example 1-a, the above derivative gives N-3-benzyloxycarbonylaminopropoxyphthalimide.

After the usual treatment with hydrazine, 3-benzyloxycarbonylaminopropoxyamine hydrochloride is obtained in the form of white crystals melting at 180° C. with a yield of 85%.

(b) 5,7-Bis(3-benzyloxycarbonylaminopropoxyimino)-6,7-dihydro-(5H)-dibenzo[a,c]cycloheptene Starting from the oxyamine prepared above and following the conditions of Example 1-b gives the title derivative in the form of an amorphous solid.

NMR: 7.4 ppm (2s) 18H (arom), 5.0 ppm (s) 4H (—CH$_2$—OCO), 4.2 to 4.05 ppm (t) 6H (—CH$_2$—) (isomers) and (N—O—$\underline{CH_2}$), 3.2 ppm (q) 4H (—$\underline{CH_2}$—NH—), 1.8 ppm (q) 4H (—CH$_2$—$\underline{CH_2}$—CH$_2$—).

(c) 5,7-Bis(3-aminopropoxyimino)-6,7-dihydro-(5H)-dibenzo[a,c]cycloheptene dihydrochloride Following the procedure of Example 18-c and using the product obtained in the previous section gives the title derivative in the form of white crystals melting at 208° C. with a yield of 85%; in TLC, it shows a single spot of Rf=0.50 in system B and Rf=0 in system A.

NMR: 8 to 8.5 ppm (m) exchangeable protons, 7.4 ppm (s broad) 8H (arom), 4.2 ppm (m) 6H (—CH$_2$—) (—O$\underline{CHH_2}$—CH$_2$—), 2.9 ppm (m) 4H (—$\underline{CH_2}$—N$\overline{H_2}$—), 2.0 ppm (m) 4H (—CH$_2$—$\underline{CH_2}$—CH$_2$).

EXAMPLE 20

5,7-Bis(Piperidin-1-ylethoxyimino)-6,7-Dihydro-(5H)-Dibenzo[a,c]Cycloheptene Dihydrochloride (a) N-(Piperidin-1-ylethoxy)phthalimide 21.3 g (0.25 mol) of piperidine are added to a solution of 54 g (0.2 mol) of N-(2-bromoethoxy)phthalimide in 800 ml of methyl ethyl ketone, in the presence of 31.5 g (0.3 mol) of sodium carbonate and 1 g of sodium iodide.

The mixture is heated under reflux for 3 hours, with vigorous stirring, and then cooled in a refrigerator in order to be filtered, and the filtrate is evaporated. The residue is taken up in chloroform for washing several times with water. This gives the title derivative with a yield of 70%; in TLC, it shows a spot of Rf=0.69 in system B. It melts at 65°-9° C.

(b) O-(Piperidin-1-ylethyl)hydroxylamine dihydrochloride 35 ml of 35% hydrochloric acid are added to a solution of 27.4 g (0.1 mol) of the derivative prepared above in 60 ml of acetic acid. The mixture is heated under reflux for 30 minutes and then cooled in a refrigerator in order to be filtered, and the filtrate is evaporated.

The residue is taken up several times in ethanol and then made into a paste with isopropyl ether. After filtration and drying, the title derivative is obtained with a yield of 75%; in TLC, it shows a spot of Rf=0.36 in system B. It melts at 178°-84° C.

(c)
5,7-Bis(piperidin-1-ylethoxyimino)-6,7-dihydro-(5H)-dibenzo[a,c]cycloheptene dihydrochloride Following the operating conditions of Example 1-b and using the hydroxylamine prepared above gives 5,7-bis(piperidin-1-ylethoxyimino)-6,7-dihydro-(5H)-dibenzo[a,c]cycloheptene after chromatography on alumina in chloroform.

The pure product is dissolved in 2 volumes of ethanol and treated with the theoretical amount of hydrochloric acid in ether solution. The addition of ether gives the title derivative in the form of crystals melting at 115°-20° C. with a yield of 55% relative to the dione; in TLC, it shows a single spot of Rf=0.55 in system B.

NMR: 7.4 ppm (s broad) 8H (arom), 4.2 ppm (m) 6H ($-CH_2-$) ($=OCH_2-$), 3.25 to 4 ppm (m) 12H ($-CH_2N-$), 1.6 ppm (s broad) 12H ($CH_2$, piperidine).

EXAMPLE 21

1,3-Bis(2-Diethylaminoethoxyimino)-2-Phenyl-(1H)-Indene-(2H) Dihydrochloride 7.12 g (32 mmol) of 2-phenyl-(1H)-indene-(2H)-1,3-dione (or phenylindanedione) are added to 200 ml of pyridine, 13.8 g (67 mmol) of diethylaminoethoxyamine hydrochloride, prepared in section a) of Example 15, are then introduced and the mixture is subsequently heated at 60°/65° C. for 15 hours, with stirring; stirring is maintained for a further 48 hours at room temperature.

The precipitate is filtered off and washed carefully with ether to give the title derivative in the form of white crystals melting at 187°/189° C.; in TLC on silica, it shows a single spot of Rf=0.40 in system B and also a single spot of Rf=0.20 in the system methylene chloride 10/acetonitrile 20/diethylamine 0.5.

NMR (in $D_2O$): 7.9 and 7.7 ppm (m coupled) 4H (arom of the indene), 7.30 ppm (s broad) 5H (2-phenyl), 5.3 ppm (s) 1H in 2-position, 4.45 ppm (m) 4H ($2\times N-O-CH_2-$), 3.5 ppm (m) 4H ($2\times -N-CH_2-$), 3.0 ppm (q) 8H ($4\times -N-CH_2-CH_3$), 1.20 ppm (t) 12H ($4\times -N-CH_2-CH_3$).

EXAMPLE 22

1,3-Bis(2-Diethylaminoethoxyimino)-(1H)-Indene-(1H) Dihydrochloride 4.25 g (29 mmol) of (1H)-indene-(2H)-1,3-dione are added to 150 ml of ethanol, and a solution of 12.1 g (59 mmol) of diethylaminoethoxyamine hydrochloride (Example 15-a) in 50 ml of ethanol is then introduced. The mixture is kept at 60° C. for 8 hours, with stirring, and stirring is then continued at 45° C. for a further 20 hours. The crystalline product is filtered off, washed with ether and recrystallized from 50 volumes of ethanol.

This gives the title derivative in the form of white crystals melting at 255° C. with a yield of 75%; in TLC on silica, it shows a single spot of Rf=0.20 in system D.

Its NMR spectrum recorded on a solution of the base in deuterated chloroform gives the following signals: 8 to 7.5 ppm (m) 4H (arom), 4.5 ppm (t) 4H ($2\times -N-OCH_2-$), 4.2 ppm (s) 2H in 2-position, 3.5 ppm (m) 4H ($2\times -N-CH_2-$), 3.0 ppm (q) 8H ($4\times -NCH_2-CH_3$), 1.20 ppm (t) 12H ($4\times -N-CH_2-CH_2-$).

EXAMPLE 23

1,3-Bis(2-Morpholinoethoxyimino)-(1H)-Indene-(2H) Dihydrochloride

The conditions of Example 22 are followed using equivalents of 2-morpholinoethoxyamine hydrochloride (synthesized according to BRITISH PATENT No. 842968).

After two crystallizations from ethanol, the title derivative is obtained in the form of white crystals melting at 254° C. with a yield of 60%; in TLC, it shows a single spot of Rf=0.30 in system B and Rf=0.30 in system D.

In NMR, the following signals are obtained: from 7.7 to 7.4 ppm (m) 4H (arom), 4.9 ppm 1H, 4.4 ppm (t) 4H ($-NOCH_2-$), 3.7 ppm 8H ($2\times -CH_2OCH_2-$), 2.75 ppm ($-N-CH_2-$).

EXAMPLE 24

1,3-Bis(2-Morpholinoethoxyimino)-2-Phenyl-(1H)-Indene-(2H) Dihydrochloride

The conditions of the previous example are followed using 2-phenylindanedione instead of indanedione.

The reaction can also be carried out in pyridine instead of ethanol. The crude product filtered off at the end of the operation is treated with an excess of an ether solution of hydrochloric acid in order to convert all the crude monohydrochloride to the dihydrochloride.

This gives the title derivative in the form of white crystals melting at 202° C. with a yield of 40%; in TLC, it shows a single spot of Rf=0.50 in system D and 0.35 in system B.

The NMR spectrum recorded in $D_2O$ shows the following characteristic signals: from 7.7 to 7.4 ppm (2m) 4H (indene), 7 ppm (s broad) 5H (phenyl), 4.89 ppm (s) 1H in 2-position, 4.3 ppm (m) 4H ($2\times -N-O-CH_2-$), from 3.8 to 3.2 ppm (2m unresolved) and 2.60 ppm (m unresolved).

EXAMPLE 25

1,3-Bis(2-Piperidin-1-ylethoxyimino)-2-Phenyl-(1H)-Indene-(2H) Dihydrochloride 11.55 g (52 mmol) of 2-phenylindane-1,3-dione are dissolved in 330 ml of pyridine, 23.9 g (110 mmol) of 2-piperidin-1-ylethoxyamine dihydrochloride are then added and the mixture is heated for 14 hours at 70° C.

The usual treatment gives the title derivative in the form of white crystals melting at 219° C. with a yield of 65%. In TLC on silica, the product shows a single spot of Rf=0.40 in system D.

NMR in $D_2O$: 7.7 to 7.4 ppm (2m) 4H (arom), 7.0 ppm (m) 5H (phenyl), 4.9 ppm (s) 1H in 2-position, 4.2 ppm (m) 4H ($2\times -N-O-CH_2-$), 3.1 to 2.8 ppm (m) 8H ($4\times -N-CH_2-$), 2.2 ppm (t) 4H ($2\times -N-CH_2-CH_2-O-$), 1.4 to 1.15 ppm (m) 12H ($6\times -CH_2-$).

EXAMPLE 26

1,3-Bis(2-Piperidin-1-ylethoxyimino-2-(4-Methoxyphenyl-(1H)-Indene-(2H) Dihydrochloride The conditions of the previous experiment are followed using 2-(4-methoxyphenyl)indane-1,3-dione, prepared according to J. Med. Chem. (1985), 28 (11), 1591, instead of 2-phenylindane-1,3-dione.

The crude product is taken up in an excess of an ether solution of hydrochloric acid to give the title derivative in the form of white crystals melting at 180°/185° C. (decomposition) with a yield of 45%; in TLC on silica, it shows a single spot of Rf=0.35 in system B and Rf=0.55 in system D.

The NMR spectrum is comparable to that of Example 25 with an additional singlet at 3.8 ppm=3H (—OCH₃).

EXAMPLE 27

1,3-Bis(2-Diethylaminoethoxyimino)-2-(4-Chlorophenyl)-(1H)-Indene-(2H) Dihydrochloride 30.75 g (0.15 mol) of diethylaminoethoxyamine hydrochloride are dissolved in 450 ml of anhydrous pyridine, and 19.25 g (75 mmol) of 2-(4-chlorophenyl)indanedione (prepared from the phthalide and chlorobenzaldehyde according to J. of Organ. Chem. 26, 3580 (1961)) are then introduced. The mixture is stirred at 100° C. for 4 hours and then at room temperature overnight. The pyridine is evaporated off under reduced pressure, the residue is taken up with dilute hydrochloric acid, the mixture is washed with ether and the base is then reprecipitated by rendering the aqueous phase alkaline with sodium hydroxide solution. It is extracted with ether and the extract is washed with water and evaporated. The residual oil is chromatographed on silica in chloroform.

The purified base, which is obtained with a yield of 78%, is converted to the hydrochloride by treatment in ethanol with an ether solution of hydrochloric acid. This gives the title derivative in the form of crystals melting at 204° C.; in TLC on silica, it shows a singe spot of Rf=0.40 in system B.

Its NMR spectrum recorded on a solution of the base in CDCl₃ gives characteristic signals comparable to those recorded in Example 21, with a singlet at 7.15 ppm instead of 7.30 ppm 4H (parachlorophenyl).

EXAMPLE 28

1,3-Bis(2-Diethylaminoethoxyimino)-2-(4-Methylphenyl)-(1H)-Indene-(2H) Dihydrochloride 18.9 g (80 mmol) of 2-(4-methylphenyl)indanedione (prepared from the phthalide and tolualdehyde according to J. of Organic Chem. 26, 3580 (1961)) are dissolved in 450 ml of pyridine, 32.8 g (160 mmol) of diethylaminoethoxyamine hydrochloride are added and the mixture is heated under reflux for 4 hours.

It is then treated following the procedure described in Example 27. The purified base, which is obtained with an almost quantitative yield, is converted to the dihydrochloride in ether. This gives the title derivative in the form of white crystals melting at 188° C.; in TLC on silica, it shows a single spot of Rf=0.35 in system B.

The NMR spectrum recorded on the base in CDCl₃ gives the following chemical shifts relative to TMS: 7.75 and 7.50 ppm (2m) 4H (indene), 7.0 ppm (s) 4H (phenyl), 5.15 ppm (s) 1H (CH in 2-position), 4.5 ppm (m) 4H (4×=N—O—$\underline{CH_2}$—), 3.25 and 2.75 ppm (2m) 12H (6×—N—$\underline{CH_2}$—), 2.30 ppm (s) 3H (CH₃-phenyl), 1.20 ppm (9) 12H (4×—CH₂$\underline{CH_3}$)

EXAMPLE 29

1,3-Bis(2-Diethylaminoethoxyimino)-2-(3,4-Methylenedioxyphenyl)-(1H)-Indene-(2H) Dihydochloride The above procedure (Example 28) is followed using 18.6 g (70 mmol) of 2-(3,4-methylenedioxyphenyl)indane-1,3-dione and 28.7 g (0.14 mol) of diethylaminoethoxyamine hydrochloride; however, the base is purified by chromatography on alumina with chloroform.

After conversion to the hydrochloride, the title derivative is obtained in the form of crystals melting at 166° C. with a yield of 85%; in TLC, Rf=0.30 in system B.

EXAMPLE 30

1,3-Bis(Ethoxycarbonylmethoxyimino)-2-Phenyl-(1H)-Indene-(2H)

12 g (100 mmol) of ethoxycarbonylmethoxyamine hydrochloride (see Example 10-a) are added to 50 mmol of 2-phenyl-(1H)-indene-(2H)-1,3-dione in 200 ml of ethanol and the mixture is heated under reflux until TLC shows that the starting material has disappeared. After evaporation, the product is purified by chromatography on a silica column. This gives the title derivative in the form of an amorphous white product showing a single spot of Rf=0.70 in the system chloroform 98/acetone 2.

NMR in CDCl₃/TMS: 7.7 and 7.4 ppm (2m) 4H (indene), 7.3 ppm (s) 5H (phenyl), 5.0 ppm (1) 1H in 2-position, 4.60 ppm (s) 4H (2×—O$\underline{CH_2}$CO—), 4.1 ppm (q) 4H (2×—$\underline{CH_2}$CH₃), 1.15 ppm (t) 6H (2×—OCH₂$\underline{CH_3}$).

EXAMPLE 31

1,3-Bis(Hydroxycarbonylmethoxyimino)-2-Phenyl-(1H)-Indene-(2H)

(a)
1,3-Bis(tert.-butoxycarbonylmethoxyimino)-2-phenyl-(1H)-indene-(2H)

The conditions of the previous example are followed using the equivalent amounts of tert.-butoxycarbonylmethoxyamine hydrochloride (see Example 11).

(b)
1,3-Bis(hydroxycarbonylmethoxyimino)-2-phenyl-(1H)-indene-(2H)

The derivative obtained in section (a) is treated by the technique described in Example 13. This gives the title derivative in the form of white crystals melting above 200° C. (decomposition), which can be converted to salts with soluble mineral bases as well as the ethanolamine and meglumine salts.

EXAMPLE 32

5,7-Bis(2-Diethylaminoethoxyimino)-6-Phenyl-6,7-Dihydro-(5H)-Dibenzo[a,c]Cycloheptene Dihydrochloride 200 mmol of diethylaminoethoxyamine hydrochloride are added to 250 ml of ethanol containing 30 g (0.1 mol) of 5,7-dioxo-6-phenyl-6,7-dihydro-(5H)-dibenzo[a,c]cycloheptene prepared by the method of B. Aleksiev (Chem. Bericht. 100, 701 [1967]). The mixture is heated under reflux for 24 hours until the starting materials have disappeared, and then treated in the usual manner. After purification of the crude base on an alumina column with chloroform and conversion to the hydrochloride in an ether solution of hydrochloric acid, the title derivative is obtained in the form of white crystals melting at 165° C.; in TLC on silica, it shows a slightly resolved spot in system B.

NMR of a solution of the base in CDCl₃ gives the following signals: 7.4 ppm (m) 8H (arom), 7.25 ppm (s broad) 5H (phenyl), 4.5 ppm (m) 4H (2×=N—O$\underline{CH_2}$—), 4.25 ppm (s) 1H (CH in 6-position), 3.2 to 2.7 ppm (m) 12H (6×—N—$\underline{CH_2}$—), 1.2 ppm (t) 12H (4×—CH₂—$\underline{CH_3}$).

Following the conditions of the previous example and using 5,7-dioxo-6-phenyl-6,7-dihydro-(5H)-dibenzo[a,c]cycloheptenes variously substituted on the 6-phenyl nucleus gives the following different products:

EXAMPLE 33

5,7-Bis(2-Diethylaminoethoxyimino)-6-(4-Fluorophenyl)-6,7-Dihydro-(5H)-Dibenzo[a,c]Cycloheptene Dihydrochloride, m.p.=176° C.

EXAMPLE 34

5,7-Bis(2-Diethylaminoethoxyimino)-6-(4-Chlorophenyl)-6,7-Dihydro-(5H)-Dibenzo[a,c]Cycloheptene Dihydrochloride, m.p.=185° C.

EXAMPLE 35

5,7-Bis(Diethylaminoethoxyimino)-6-(4-Methoxyphenyl)-6,7-Dihydro-(5H)-Dibenzo[a,c]Cycloheptene Dihydrochloride, m.p.=155° C.

EXAMPLE 36

5,7-Bis(Diethylaminoethoxyimino)-6-(4-Methylphenyl)-6,7-Dihydro-(5H)-Dibenzo[a,c]Cycloheptene Dihydrochloride, m.p.=170° C.

EXAMPLE 37

Study of the Effects on the Platelet Aggregation (Platelet-Rich Human Plasma) Induced in Vitro By: ADP, Collagen or Arachidonic Acid Blood samples from volunteer donors are treated and adjusted to a platelet concentration of $300,000/cm^2$ and then incubated with different concentrations of the test products. Aggregation is induced by 2.0 μg/ml of ADP or by 10.0 μg/ml of collagen.

The measurements are made using a Bryston-type aggregometer—or CHRONOLOG. The changes in optical density are noted and the values of the concentrations which cause a 50% inhibition are calculated. These values are reported in the following table:

| DERIVATIVE | IC$_{50}$ in μg/ml | |
|---|---|---|
| | Inductor: ADP | Inductor: collagen |
| Ex. 1 | 650 | 800 |
| 2 | — | 800 |
| 3 | 620 | 500 |
| 4 | 600 | 420 |
| 5 | 420 | 650 |
| 6 | 460 | 600 |
| 7 | 600 | 600 |
| 8 | 650 | 800 |
| 9 | 600 | 600 |
| 10 | 400 | 650 |
| 11 | 200 | 320 |
| 12 | 450 | 670 |
| 13 | 400 | 450 |
| 14 | 460 | 600 |
| 15 | 10 | 24 |
| 16 | 16 | 22 |
| 17 | 10 | 16 |
| 18 | 40 | 50 |
| 19 | 100 | 175 |
| 20 | 80 | 120 |
| 21 | 24 | 40 |
| 22 | 160 | 145 |
| 23 | 420 | 350 |
| 24 | 210 | 340 |
| 25 | 20 | 38 |
| 26 | 18 | 24 |
| 27 | 28 | 40 |
| 28 | 40 | 62 |
| 29 | 100 | 110 |
| 30 | 210 | 150 |
| 31 | — | 250 |

-continued

| DERIVATIVE | IC$_{50}$ in μg/ml | |
|---|---|---|
| | Inductor: ADP | Inductor: collagen |
| 32 | 18 | 20 |
| 33 | 22 | 12 |
| 34 | 24 | 40 |
| 35 | 16 | 25 |

What is claimed is:

1. Beta-bis(alkoxyimino)cycloalkene derivative with conjugated double bonds, corresponding to the following general formula:

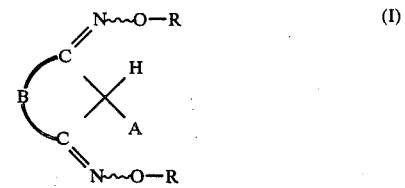

in which:

A represents hydrogen, a phenyl group or a phenyl group substituted by:
  one or two halogen atoms,
  one or two lower alkyl radicals,
  one or two alkoxy radicals selected from the group consisting of methoxy, ethoxy, propoxy, isopropoxy, butoxy and tert.-butoxy groups,
  one or more substituents selected from the group consisting of nitro, cyano, dimethylamino and diethylamino groups,
  several substituents selected form each of the different groups above, or
  an o-methylenedioxy or o-ethylenedioxy group;

R represents:
  a linear or branched saturated or unsaturated alkyl radical containing from 1 to 16 carbon atoms,
  a cycloalkylalkyl or cycloalkyl radical which contains a total of 4 to 16 carbon atoms and whose ring contains from 3 to 8 carbon atoms,
  a phenyl or phenylalkyl radical, the alkyl unit containing from 1 to 3 methylene linkages,
  a linear or branched alkyl radical containing from 1 to 6 carbon atoms and substituted by —NR$_1$R$_2$, where R$_1$ and R$_2$, which are identical or different, are hydrogen atoms or linear or branched alkyl groups containing from 1 to 4 carbon atoms and optionally substituted by a hydroxyl, methoxy or ethoxy group,
  a heterocycle containing from 5 to 7 ring members and 1 or 2 heteroatoms selected from the group consisting of nitrogen, sulfur and oxygen, the said heterocycle being connected by an alkylene linkage containing from 1 to 6 carbon atoms, or
  a saturated or unsaturated linear or branched alkyl radical containing from 1 to 16 carbon atoms substituted by:
    a group CN or
    a group —COOQ, Q being hydrogen, a linear or branched alkyl radical containing from 1 to 6 carbon atoms or a phenylmethyl or phenyl radical, these phenyl rings being optionally substituted by a halogen, a cyano group, a methyl group, a methoxy group or a trifluoromethyl group; and B is selected from the group consisting of a phenyl group and a biphenyl group, B being conjugated with the imino groups as represented in the following formulas (a) and (b):

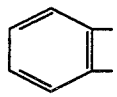
(a)

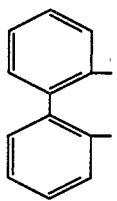
(b)

and their pharmacologically acceptable salts in cases where R contains a salifiable group.

2. A derivative as claimed in claim 1, which consists of a mixture of the ZZ, ZE and EE isomers.

3. A derivative as claimed in claim 1, which consists of a pure ZZ, ZE or EE isomer.

4. Derivatives as claimed in any one of claims 1 to 3, wherein R represents a radical alkyl-COOQ, Q being hydrogen or a $C_1$ to $C_6$ alkyl.

5. Derivatives as claimed in any one of claims 1 to 3, wherein R represents a five-membered or six-membered heterocycle containing one or two heteroatoms which can be nitrogen, sulfur or oxygen, bonded to a methylene or ethylene group.

6. Derivatives as claimed in any one of claims 1 to 3, wherein R represents a diethylaminoalkyl radical, the alkyl group containing from 2 to 6 carbon atoms.

7. Derivatives as claimed in any one of claims 1 to 3 and 6, wherein R represents the diethylaminoethyl group.

8. Derivatives as claimed in any one of claims 1 to 3, wherein $R_1$ and $R_2$ each represent a hydrogen atom.

9. Derivatives as claimed in any one of claims 1 to 3, wherein A represents a 4-substituted phenyl.

10. Derivatives as claimed in any one of claims 1 to 3, wherein A represents a phenyl substituted in the 4-position by a halogen.

11. Derivatives as claimed in any one of claims 1 to 3, wherein A represents an unsubstituted phenyl.

12. Derivatives as claimed in any one of claims 1 to 3, wherein A is hydrogen.

13. Derivatives as claimed in any one of claims 1 to 3 and 5, wherein R is a 6-membered heterocycle containing one or two nitrogen atoms connected by an alkylene linkage.

14. Derivatives as claimed in any one of claims 1 to 3, 6 and 7, wherein A is an unsubstituted phenyl.

15. The bis-O-(diethylaminoethyl)oxime of 5,7-dioxo-6,7-dihydro-(5H)-dibenzo[a,c]cycloheptene.

16. Drugs consisting essentially of at least one of the derivatives as claimed in claim 1 and a pharmaceutically acceptable carrier.

* * * * *